(12) United States Patent
Iketaki et al.

(10) Patent No.: US 8,947,658 B2
(45) Date of Patent: Feb. 3, 2015

(54) NONLINEAR OPTICAL MICROSCOPE AND NONLINEAR OPTICAL MICROSCOPY

(75) Inventors: Yoshinori Iketaki, Tokyo (JP); Hideaki Kano, Tokyo (JP)

(73) Assignees: Olympus Corporation, Tokyo (JP); The University of Tokyo, Tokyo (JP)

( * ) Notice: Subject to any disclaimer, the term of this patent is extended or adjusted under 35 U.S.C. 154(b) by 103 days.

(21) Appl. No.: 13/610,563

(22) Filed: Sep. 11, 2012

(65) Prior Publication Data
US 2013/0083322 A1 Apr. 4, 2013

(30) Foreign Application Priority Data

Sep. 29, 2011 (JP) ................................ 2011-215477

(51) Int. Cl.
| | |
|---|---|
| G01J 3/44 | (2006.01) |
| G01N 21/65 | (2006.01) |
| G01J 3/10 | (2006.01) |
| G02B 21/00 | (2006.01) |
| G02B 21/08 | (2006.01) |
| G02B 21/14 | (2006.01) |
| G02B 27/44 | (2006.01) |

(52) U.S. Cl.
CPC . *G01N 21/65* (2013.01); *G01J 3/44* (2013.01); *G01J 3/10* (2013.01); *G02B 21/0004* (2013.01); *G02B 21/082* (2013.01); *G02B 21/14* (2013.01); *G02B 27/44* (2013.01); *G01N 2021/653* (2013.01)
USPC .......................................................... 356/301

(58) Field of Classification Search
USPC ............................................ 356/301, 72–73
See application file for complete search history.

(56) References Cited

U.S. PATENT DOCUMENTS

| | | | |
|---|---|---|---|
| 6,667,830 B1 | 12/2003 | Iketaki et al. | |
| 7,202,953 B1 * | 4/2007 | Mueller et al. | ................ 356/445 |

FOREIGN PATENT DOCUMENTS

JP 3350442 B2 11/2002

OTHER PUBLICATIONS

"Investigation of the center intensity of first- and second-order Laguerre-Gaussian beams with linear and circular polarization": Yoshinori Iketaki et al.: Optics Letter. vol. 32, No. 16: Aug. 15, 2007: pp. 2357-2359.
"Electromagnetic diffraction in optical systems II. Structure of the image field in an aplanatic system": B. Richards et al.: Proceedings of The Royal Society: Series A: Mathematical and Physical Sciences No. 1274: Dec. 15, 1959: vol. 253: pp. 358-367.

(Continued)

*Primary Examiner* — Abdullahi Nur
(74) *Attorney, Agent, or Firm* — Holtz, Holtz, Goodman & Chick PC

(57) ABSTRACT

Provided is a nonlinear optical microscope capable of improving the spatial resolution. The nonlinear optical microscope includes: an illuminating part for irradiating, through an objective lens, a sample with at least two colors of illumination light beams spatially and temporally overlapping each other; and a detecting part for detecting signal light generated from the sample due to nonlinear optical effect, the signal light resulting from the irradiation of the sample with the at least two colors of illumination light beams, in which the illuminating part irradiates the sample with the two colors of illumination light beams in which at least one of the illumination light beams has a wavefront distribution different from a wavefront distribution of the other one of the illumination light beams.

19 Claims, 12 Drawing Sheets

(56) References Cited

OTHER PUBLICATIONS

"Generation of a doughnut-shaped beam using a spiral phase plate": Review of Scientific Instruments: vol. 75, No. 12: Dec. 2004: pp. 5131-5135.

"Annular aperture-detected coherent anti-Stokes Raman scattering microscopy for high contrast vibrational imaging": Jian Lin et al.: Appl. Phys. Lett. 97, 083071 (2010).

"Edge-Enhancement Fourier Transform X-ray Microscopy Using a Laguerre-Gaussian Zoneplate": Nandor Bokor et al.: Opitlca Review: vol. 17, No. 2 (2010): pp. 79-83.

"Ultrabroadband multiplex CARS Microspectroscopy Using a Supercontinuum Light Source": Hideaki Kano et al.: ICORS2006, Yokohama (Aug. 2006).

"Coherent Anti-Stokes Raman Scattering Microscopy: Instrumentation, Theory, and Applications": Ji-Xin Cheng et al.: J. Phys. Chem. B 2004, 108: pp. 827-840.

"Coherent Raman Imaging of Human Living Cells Using a Supercontinuum Light Source": Hideaki Kano et al.: Japanese Journal of Applied Physics: vol. 46, No. 10A, 2007: pp. 6875-6877.

"Ultrabroadband multiplex CARS microspectroscopy and imaging using a subnanosecond supercontinuum light source in the deep near infrared": Masanori Okuno et al.: Optics Letters: vol. 33, No. 9: May 1, 2008: pp. 923-925.

\* cited by examiner (a) LEFT-HANDED CIRCULARLY POLARIZED LIGHT (b) LINEARLY POLARIZED LIGHT (c) RIGHT-HANDED CIRCULARLY POLARIZED LIGHT (a)

(b)

(a)

(b)

(a)

(b)

NONLINEAR OPTICAL MICROSCOPE AND NONLINEAR OPTICAL MICROSCOPY

CROSS-REFERENCE TO RELATED APPLICATION

The present application claims priority from Japanese Application No. 2011-215477, filed on Sep. 29, 2011, the content of which is incorporated herein by reference.

TECHNICAL FIELD

The present invention relates to a nonlinear optical microscope and nonlinear optical microscopy.

RELATED ART

The technique of optical microscopes has a long history, during which various types of optical microscopes have been developed. In recent years, as a result of progress in the peripheral technologies such as laser technology and electronic imaging technology, high-performance optical microscope systems have been developed. In such a background, high-performance optical microscopes using various spectral processes have been proposed, so that not only the shape of a sample can be analyzed but also a molecule included in the sample can be identified and/or the structure thereof can be analyzed.

As one example of these spectral processes, there is Raman spectroscopy in which photoresponse from a biological sample or an industrial material is observed without staining the biological sample or the industrial material to reveal the structure thereof. Raman spectroscopy is expected to be applied to the field of a microscope. Raman spectroscopy is based on a type of nonlinear optical effect referred to as Raman effect. When light at high photon flux is scattered by a molecule or an atom, a quantum state of the molecule is changed and energy of the entire system is changed accordingly. At that time, the changed energy shifts to the scattered photon, whereby, light having a different wavelength from that of the incident light appears. Such a phenomenon is referred to as Raman scattering.

Raman scattering may be implemented by using monochromatic light or polychromatic light. There are three types of Raman scattering with the use of monochromatic light, that is, (1) non-resonant Raman scattering, (2) true resonance Raman scattering, and (3) preresonance Raman scattering, and one type of Raman scattering with the use of polychromatic light, that is, (4) coherent Raman scattering. Hereinafter, these types of Raman scattering are further described in detail with reference to FIGS. 13 and 14.

(1) Non-Resonant Raman Scattering

FIG. 13($a$) is an energy diagram for illustrating non-resonant Raman scattering. Non-resonant Raman scattering can be explained by second-order perturbation theory from a viewpoint of an atom and a molecule. Specifically, as illustrated in FIG. 13($a$), non-resonant Raman scattering corresponds to a kind of two-photon process in which a virtual quantum level of S (imaginary) is assumed. In this two-photon excitation process, molecules in a lowest electronic state and a lowest rovibrational level, that is, in the ground state (state $S_0$) are once excited to a virtual quantum level S (imaginary) by, for example, extremely strong laser light and afterwards, de-excited to a high rovibrational level ($V_2$) of the lowest electronic state. As a result, as is apparent from FIG. 13($a$), the incident light provides an atom or a molecule with photon energy of ($E_f$–$E_0$), whereby light after non-resonant Raman scattering loses photon energy accordingly and the light is scattered such that the initial wavelength $\lambda_1$ thereof is apparently changed to a longer wavelength of $\lambda_2$. In general, in a two-photon process based on a virtual quantum level including non-resonant Raman scattering, transition probability is extremely small, and therefore, in order to induce this process, a super short pulsed laser on the order of femtoseconds may be required.

(2) True Resonance Raman Scattering

FIG. 13($b$) is an energy diagram explaining true resonance Raman scattering. True resonance Raman scattering is a scattering process in which non-resonance Raman scattering satisfies a specific condition that, as illustrated in FIG. 13($b$), S (imaginary) coincides with the actual electronically-excited state $S_1$. This case corresponds to a process in which a molecule of the ground state $S_0$ is excited to the actual electronically-excited state $S_1$ and then de-excited to a high rovibrational level ($V_2$) of a lowest electronic state. Therefore, the process, as illustrated in FIG. 13($b$), apparently corresponds to a process in which fluorescence of $\lambda_2$ was emitted after $S_0 \rightarrow S_1$ excitation. Since this true resonance Raman scattering utilizes the actual quantum states, scattering probability is extremely high and Raman scattering can be achieved with markedly high light intensity as compared with non-resonant Raman scattering.

(3) Preresonance Raman Scattering

FIG. 13($c$) is an energy diagram explaining preresonance Raman scattering. Preresonance Raman scattering has a property intermediate between true resonance Raman scattering and non-resonant Raman scattering. Specifically, this is a case where the level of S (imaginary) exists in the vicinity of the electronically-excited state $S_1$.

(4) Coherent Raman Scattering

FIG. 14 are views for illustrating coherent Raman scattering. FIG. 14($a$) is an energy diagram of Coherent Anti-Stokes Raman Scattering (hereinafter, also referred to as CARS as appropriate) and FIG. 14($b$) is an energy diagram of Coherent Stokes Raman Scattering (hereinafter, also referred to as CSRS as appropriate). Coherent Raman scattering is one of the third-order nonlinear optical response processes, and various studies have been made thereon in both aspects of experiments and theories.

This coherent Raman scattering generally uses two kinds of laser light (one is $\omega_1$ light and the other is $\omega_2$ light) having different angular frequencies. The laser light ($\omega_1$ light (pump light) and $\omega_2$ light (probe light)) which firstly interacts with a molecule is also referred to as pump light and Stokes light. When the angular frequency difference between these two types of incident light coincides with the angular frequency $\Omega$ of a vibration mode of sample molecules, a large number of the sample molecules are excited in a resonant vibration mode and with the phases thereof corresponding to each other, i.e., coherently. Since the generated vibration polarization is maintained during the phase relaxation time, the molecules interact with $\omega_1$ light during the phase relaxation time, so that coherent Raman scattered light derived from the third nonlinear polarization can be taken out.

More specifically, by changing delay time between the pump light and probe light, as well as between Stokes light and probe light, information about phase relaxation time of molecule vibration can be obtained. In particular, as shown in FIG. 14($a$), the Raman scattered light having frequency increased by +$\Omega$ is referred to as CARS. In addition, as shown in FIG. 14($b$), the Raman scattered light having frequency decreased by –$\Omega$ is referred to as CSRS. In the case of CARS, since signal light can be detected on a shorter wavelength side than that of excitation light, in particular, CARS is less likely to be affected by the background and the like caused by self fluorescence, whereby signal light can be detected with an excellent S/N ratio.

In general, strong CARS signals are generated through resonance with the molecule frequency of a specific chemical group, and thus the CARS signals thus generated may be referred to as resonant CARS signal. In contrast, CARS signals broadly generated in a wavelength region (frequency region) which is not resonant with the molecule frequency are weak in intensity as being obtained through a kind of non-resonant/nonlinear optical process, and referred to as non-resonant CARS signals.

In recent years, the CARS process has started to be widely applied to spectroscopic microscopes and the like. In addition, in microscopy for capturing CARS signals, that is, in the CARS microscopy, since a biological sample can be observed without being stained (see, for example, J. Phys. Chem. B 2004, 108, 827-840, Jpn. J. Appl. Phys. 46(2007)6875), the marketing prospect thereof is very promising.

DISCLOSURE OF THE INVENTION

In the CARS process, two or more colors of light sources are used to induce a tertiary nonlinear optical effect. For example, when two colors of light sources are used, a Raman scattered signal, namely, a signal intensity I that can be obtained from a sample is proportional to a product of a power of pump light intensity and probe light intensity on the light-collecting surface of the sample, as given in Expression (1), assuming that pump light intensity is $P_1$ and probe light intensity is $P_2$.

$$I \propto P_1^2 P_2 \tag{1}$$

Here, on the assumption that the collected beams have an electric field distribution defined as a Gaussian function as given in Expression (2), the signal intensity I is represented by Expression (3).

$$P_n \propto \exp\left(-\frac{x^2}{a_n^2}\right) \tag{2}$$

$$I \propto \exp\left[-\left(\frac{2}{a_1^2} + \frac{1}{a_2^2}\right)x^2\right] \tag{3}$$

Based on Expression (3), the full width at half maximum ($\Gamma$) of the signal intensity I is given in Expression (4).

$$\Gamma = \log 2 a_1 a_2 \sqrt{\frac{1}{(2a_1^2 + a_2^2)}} \tag{4}$$

In Expressions (3) and (4), $a_1$ and $a_2$ are constants each representing the divergence of the pump light and the probe light, respectively. For example, a full width at half maximum ($\gamma$) of the electric field intensity distribution of an ordinary collected Gaussian beam is given in Expression (5).

$$\gamma = \log 2 a_1 \tag{5}$$

Comparing Expression (4) and Expression (5), $\Gamma$ is smaller than $\gamma$ ($\Gamma < \gamma$), which means that a beam size, namely, a point spread function is reduced as compared to a case of using an ordinary monochromatic illumination. Therefore, the spatial resolution appears to be seemingly increased.

However, since the CARS microscopy employs near-infrared light as illumination light, which does not increase the absolute spatial resolution, failing to attain the diffraction limit of an optical microscope, which is 200 nm. As a result, in the CARS microscopy, although importance is attached to the capability of identifying the chemical composition of a sample, its low resolution hinders the practical utilization and proliferation thereof. The same problem also arises in other microscopy technologies with the use of polychromatic light including, for example, multiplexed two-photon microscopy.

A nonlinear optical microscope according to the present invention includes:

an illuminating part, which includes an objective lens, for irradiating, through the objective lens, a sample with at least two colors of illumination light beams that are different from each other in wavelength and overlap each other spatially and temporally; and a detecting part for detecting signal light generated from the sample due to nonlinear optical effect, the signal light resulting from the irradiation of the sample with the at least two colors of illumination light beams, in which the illuminating part irradiates the sample with the two colors of illumination light beams in which at least one of the illumination light beams has a wavefront distribution different from a wavefront distribution of the other one of the illumination light beams.

In an embodiment of the nonlinear optical microscope according to the present invention, the detecting part detects the signal light generated from the sample due to at least one of nonlinear optical effects including multiphoton excitation, Coherent Anti-Stokes Raman Scattering, and Coherent Stokes Raman Scattering.

In an embodiment of the nonlinear optical microscope according to the present invention, the illuminating part includes a phase modulation element and a polarization element, the phase modulation element modulating each of the at least two colors of illumination light beams to be irradiated onto the sample into a Laguerre-Gaussian beam, the polarization element polarizing each of the at least two colors of illumination light beams to be irradiated onto the sample into circularly-polarized light.

In an embodiment of the nonlinear optical microscope according to the present invention, the illuminating part includes a mask filter in an annular shape which is disposed in an optical path along which the at least two colors of illumination light beams are made incident as spatially and temporally overlapping each other.

In an embodiment of the nonlinear optical microscope according to the present invention, the detecting part includes: a collimator lens for converting signal light generated from the sample into parallel light beams; and a mask filter in an annular shape disposed in an optical path of the parallel light beams, and detects the signal light that has passed through the mask filter.

Further, nonlinear optical microscopy according to the present invention includes:

an illuminating step of irradiating, through an objective lens, a sample with at least two colors of illumination light beams that are different from each other in wavelength and overlap each other spatially and temporally; and a detecting step of detecting signal light generated from the sample due to nonlinear optical effect, the signal light resulting from the irradiation of the sample with the at least two colors of illumination light beams, in which the two colors of illumination light beams irradiated onto the sample in the illuminating step include at least one of the illumination light beams having a wavefront distribution different from a wavefront distribution of the other one of the illumination light beam.

In an embodiment of the nonlinear optical microscopy according to the present invention, the detecting step includes detecting the signal light generated from the sample due to at least one of nonlinear optical effects including multiphoton excitation, Coherent Anti-Stokes Raman Scattering, and Coherent Stokes Raman Scattering.

In an embodiment of the nonlinear optical microscopy according to the present invention, the at least two colors of illumination light beams to be irradiated onto the sample in the illuminating step each are a Laguerre-Gaussian beam.

In an embodiment of the nonlinear optical microscopy according to the present invention, the at least two colors of illumination light beams to be irradiated onto the sample in the illuminating step each are an annular illumination light beam.

In an embodiment of the nonlinear optical microscopy according to the present invention, the at least two colors of illumination light beams to be irradiated onto the sample in the illuminating step each are a circularly-polarized light beam.

In an embodiment of the nonlinear optical microscopy according to the present invention, the detecting step includes detecting the signal light generated from the sample by a confocal method.

BEST MODES FOR CARRYING OUT THE INVENTION

First, an embodiment of nonlinear optical microscopy according to the present invention is described by taking, as an example, CARS microscopy.

The CARS microscopy according to an embodiment of the present invention mainly employs two methods including: wavefront control; and pupil function operation. These methods can be combined so as to improve the spatial resolution, and also to significantly improve S/N ratio, as will be described later. The present invention has been made by focusing on signal generation specific to the CARS microscopy. That is, in the CARS microscopy, it is necessary to fill a requirement that the illumination light beams involved have electric fields that are polarized in the same direction. In other words, no CARS signal is generated when light beams polarized in different directions overlap each other. The embodiment of the present invention focuses on this feature.

Figure 1:
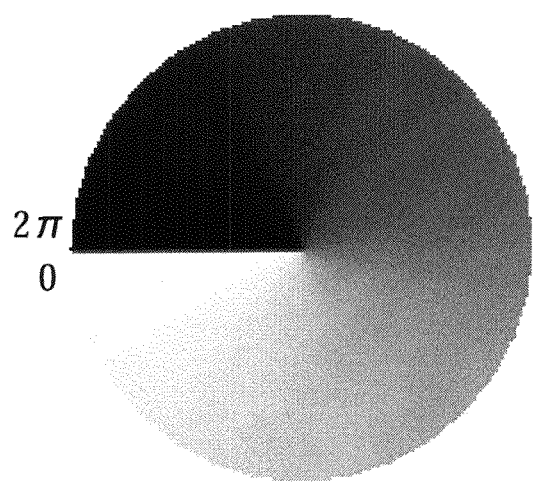
FIG. 1 is a view for illustrating a phase distribution of a Laguerre-Gaussian beam.
Figure 2:
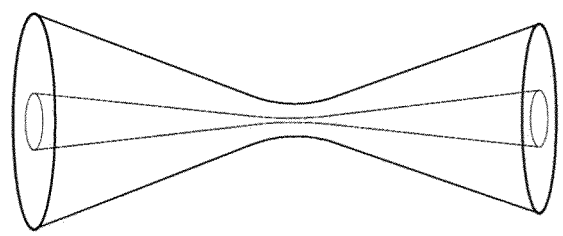
FIG. 2 illustrates a beam shape to be obtained when the Laguerre-Gaussian beam is collected by an objective lens with a small numerical aperture.

Specifically, focused first are the characteristics of a Laguerre-Gaussian beam. As shown in FIG. 1, the Laguerre-Gaussian beam has a pupil phase distribution that continuously changes about the beam optical axis. The phase undergoes change from 0 to $2\pi$ during one revolution about the optical axis. When this Laguerre-Gaussian beam is collected by an objective lens with a small numerical aperture (for example, NA of less than 0.5), the phase is generally inverted at point-symmetric positions about the optical axis, so that the electric field intensity is canceled out. As a result, the collected light beam takes a doughnut-like shape as illustrated in FIG. 2.

Figure 3:
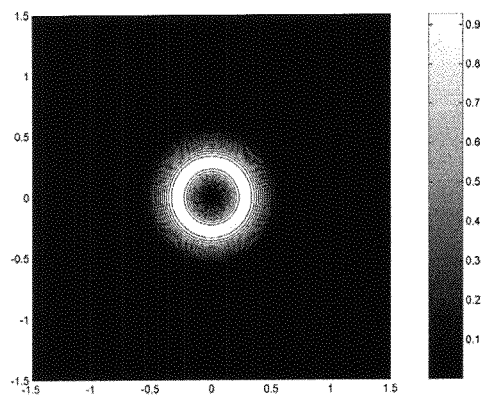
FIGS. 3(a) to 3(c) illustrate beam shapes to be obtained, according to the polarization states, when the Laguerre-Gaussian beam is collected by an objective lens with a large numerical aperture.
Figure 3:
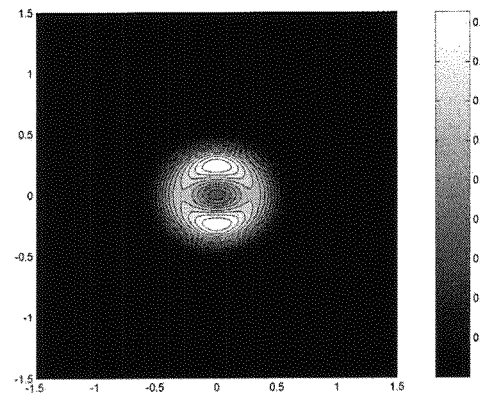
Figure 3:
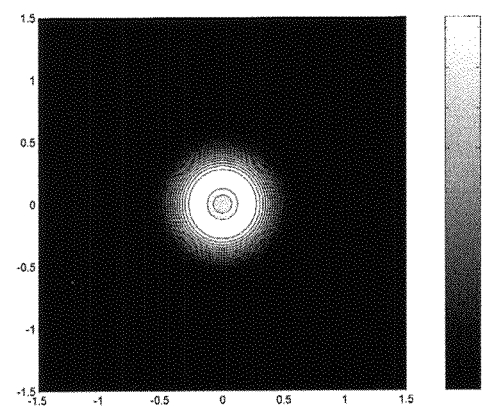

However, when the Laguerre-Gaussian beam is collected with an objective lens with a large numerical aperture (for example, NA of equal to or larger than 0.7), the light-collecting pattern is known to change depending on the polarization state (see, for example, Opt. Lett. 32(2007)2357). For example, when a Laguerre-Gaussian beam having three different polarization states including: two kinds of circularly polarized light that are different from each other in polarization rotation direction; and linearly polarized light, the collected light beams take different shapes as shown in, for example, FIGS. 3(a) to 3(c). FIG. 3(a) shows a collected light beam shape to be obtained for a circularly-polarized light having a rotation direction which coincides with the phase rotation direction, FIG. 3(b) shows a collected light beam shape to be obtained for a linearly-polarized light which is subjected to phase rotation, and FIG. 3(c) shows a collected light beam shape to be obtained for a circularly-polarized light having a rotation direction which is opposite to the phase rotation direction.

As is apparent from FIGS. 3(a) to 3(c), in particular, from FIG. 3(c), the electric field intensity at the center of the collected light beam is no longer zero in the case where the phase rotation direction of the Laguerre-Gaussian beam is opposite to the polarization rotation direction. This point is described in below in terms of wavefront control.

Figure 4:
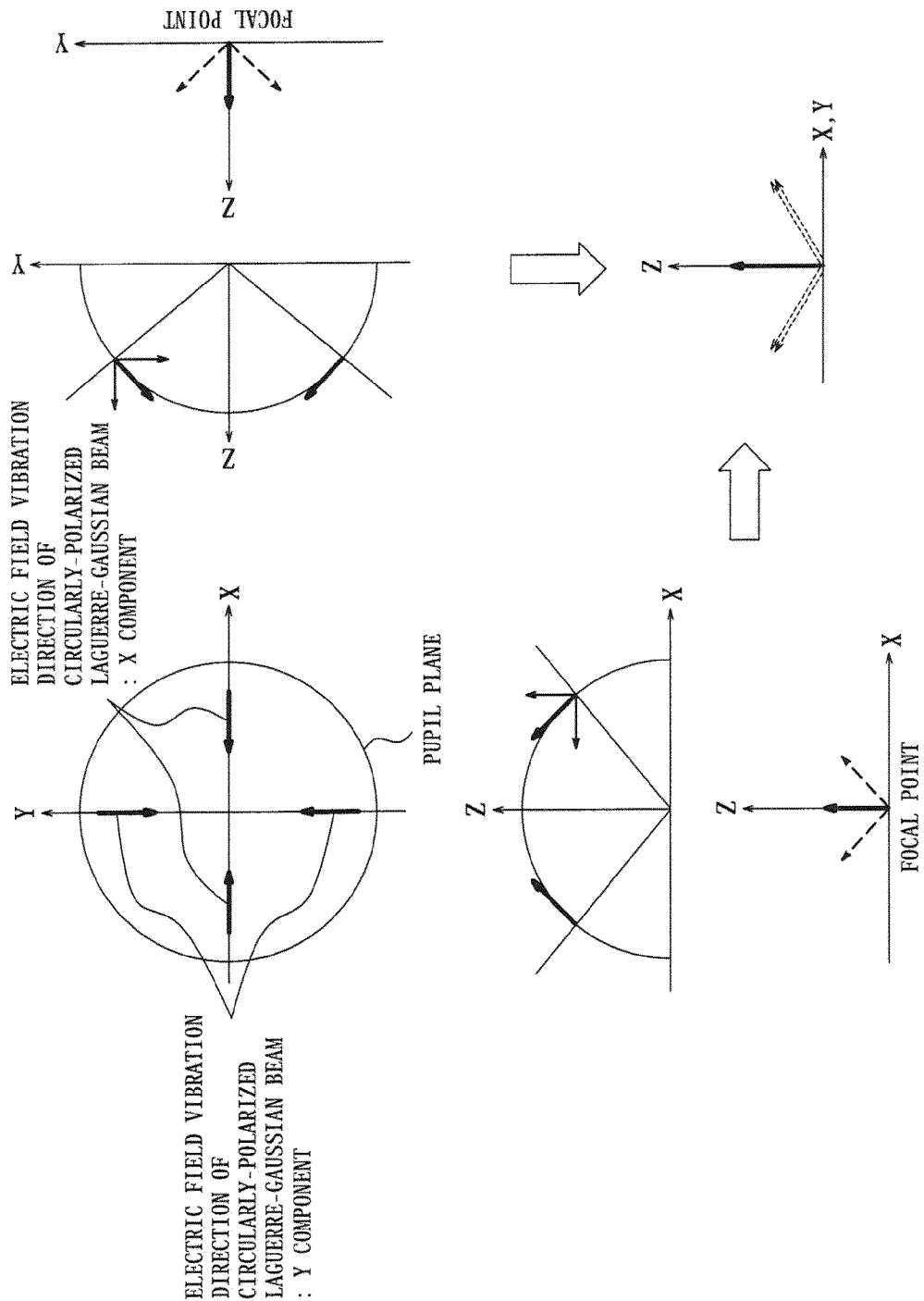
FIG. 4 is a view for illustrating a state of an electric field at the converging point of a Laguerre-Gaussian beam which is collected by an objective lens with a large numerical aperture.

When the Laguerre-Gaussian beam is collected by an objective lens with a large numerical aperture, the electric field of the illumination light includes, at a light-collecting point, a component parallel to the optical axis, as illustrated in FIG. 4. That is, the electric field of the illumination light can be separated into an optical axis component (z component) and a focal plane component (x-y component). Therefore, in particular, when the rotation direction of the electric field of a circularly-polarized light turns opposite to the rotation direction of the phase, the electric fields in the z direction generated by the two kinds of linearly-polarized light components which form the circularly-polarized light are combined together, to thereby generate a large z-component electric field at the focal point. In particular, light that has passed through an annular zone portion at the edge of the pupil plane in the objective lens greatly contributes to the generation of z components, which has an effect similar to a form of apodization.

Figure 5:
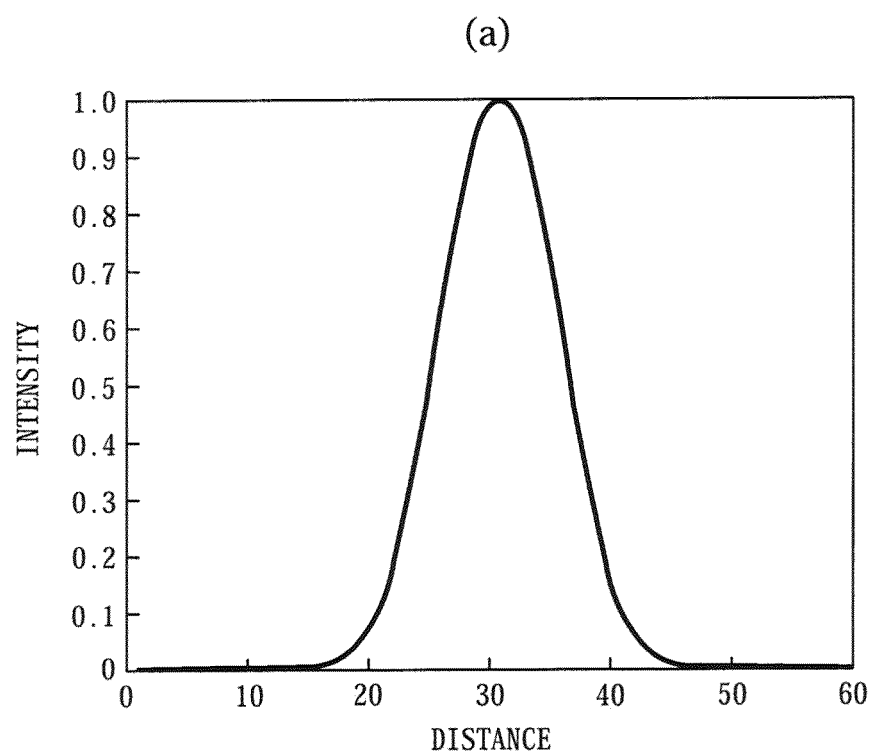
FIGS. 5(a) and 5(b) are graphs showing, in comparison, the point spread functions on a focal plane obtained for linearly-polarized light and circularly-polarized light, respectively.
Figure 5:
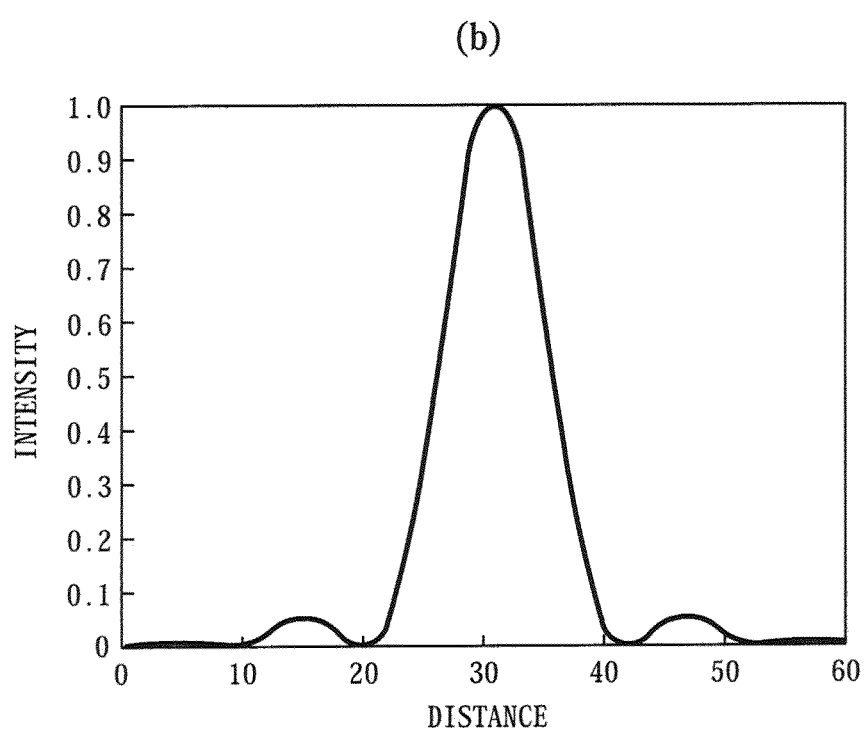

In this manner, the full width at half maximum of the point spread function of the z component on the focal plane becomes narrower in the case of the circularly-polarized light shown in FIG. 5(b) than in the case of the ordinary linearly-polarized light shown in FIG. 5(a). The results shown in FIGS. 5(a) and 5(b) were both obtained through specific calculation using Debye's integral equation (Proc. Royal. Soc. A253(1959)358) on the assumption that that the numerical aperture of the objective lens was 0.9. In this case, the full width at half maximum obtained for the circularly-polarized light is found to be narrower than the full width at half maximum obtained for the linearly-polarized light by about 30%.

Meanwhile, in the CARS microscopy, a sample generates a CARS signal only when electric fields are polarized in the same direction. Here, when the pump light and the probe light are each modulated into a Laguerre-Gaussian beam while being subjected to the circular polarization control as described above, the pump light and the probe light each have the phase thereof rotated at a speed corresponding to the frequency of each light, so that the two color light beams have different rotation speeds in the electric field within the focal plane. As a result, the two color light beams have the electric fields polarized in relatively random directions. In other words, the two color light beams are different from each other in wavefront distribution.

For this reason, at the time average, the plane components in the polarization directions of the pump light and the probe light are always different from each other, and hence no CARS signal is generated from a region where the plane components overlap each other. Therefore, CARS signals are generated only from a region where the z components having the same polarization direction overlap each other. As a result, as illustrated in FIG. 5(b), the full width at half maximum of the electric field intensity which contributes to the generation of CARS signal becomes smaller as compared to the case of an ordinary light collecting method.

Here, in view of Expression (1), the point spread function of effective CARS signals is obtained as a product of the electric field intensities of the z components of the pump light and the probe light. Therefore, Expression (3) shows that the point spread function thus obtained has a full width at half maximum narrower than that of a conventional CARS signal, and therefore the spatial resolution is improved. Further, the CARS microscopy according to an embodiment of the present invention additionally provides, in addition to the wavefront control as described above, pupil function operation, namely, apodization effect. Specifically, components in the center in the pupil plane are removed by a stopper. In this manner, the z components in the focal plane can be increased in purity, which further narrows the full width at half maximum, to thereby improve the spatial resolution.

In the following, a nonlinear optical microscope according to an embodiment of the present invention is described by taking, as an example, a CARS microscope.

Figure 6:
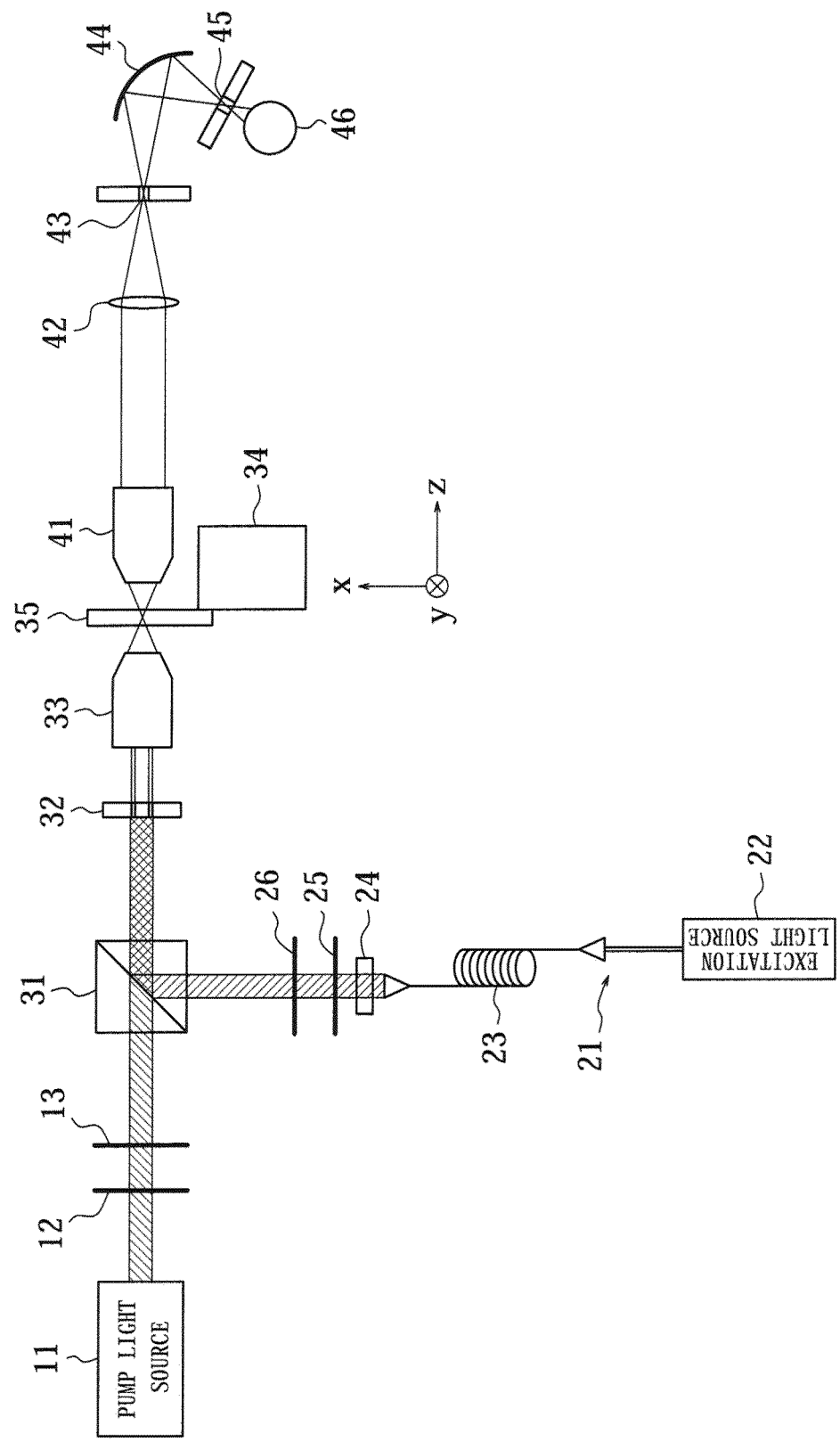
FIG. 6 illustrates a schematic configuration of a CARS microscope according to an embodiment of the present invention.

FIG. 6 illustrates a schematic configuration of a CARS microscope according to an embodiment of the present invention. The CARS microscope of FIG. 6 uses illumination light beams of two colors, and includes a pump light source 11 and a probe light source 21. The pump light source 11 includes, for example, an Nd:YVO4 pulse laser for emitting short-pulse light on the order of picoseconds, or an Nd:YAG pulse laser for emitting short-pulse light on the order of nanoseconds, and emits linearly-polarized light with a wavelength of 1,064 nm as pump light which serves as a fundamental wave for the short-pulse light.

Figure 7:
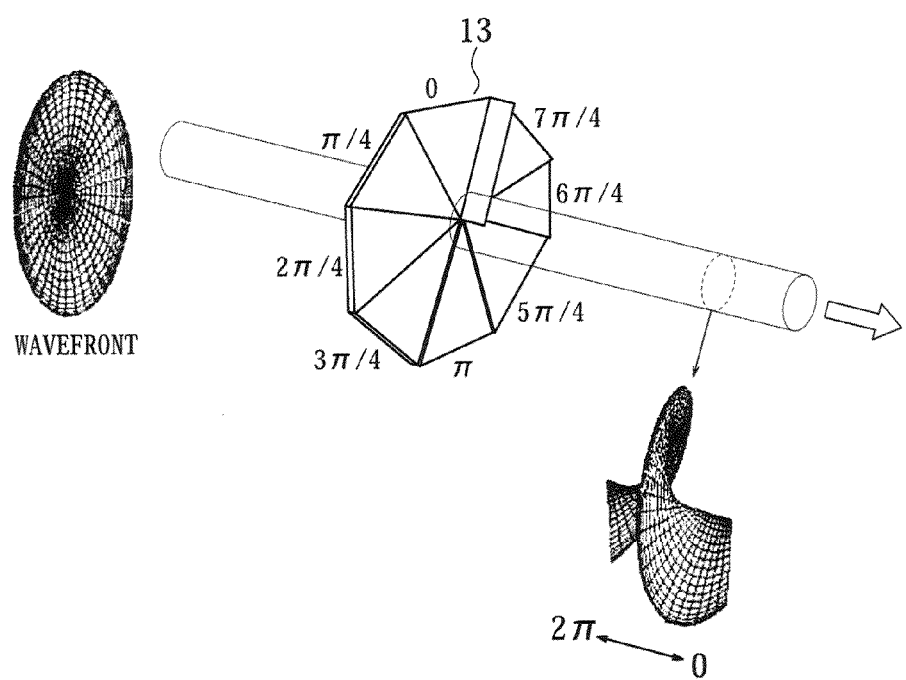
FIG. 7 is a perspective view illustrating a schematic configuration of an example of the phase plate of FIG. 6.

The pump light emitted from the pump light source 11 is converted into circularly-polarized light by a quarter wavelength plate 12 serving as a polarization element, and further converted into a Laguerre-Gaussian beam by a phase plate 13 serving as a phase modulation element, so as to be incident on a beam combiner 31. The phase plate 13 is configured to cause the phase difference of the pump light to revolve about the optical axis of the pump light by, for example, $2\pi$. For example, as schematically illustrated in FIG. 7, the phase plate 13 is formed of a glass substrate which is spirally etched so as to have independent eight regions about the optical axis which are different from one another in phase by $\pi/4$. Alternatively, a transparent thin film may be spirally vapor-deposited on the glass substrate so as to effect optical path phase differences (see, for example, Rev. Sci. Instrum. 75(2004) 5131).

The probe light source 21 includes: a super-continuum laser which includes an excitation light source 22 and a photonic crystal fiber 23; and a line filter 24. The supercontinuum laser receives an excitation light pulse having a large peak-to-peak value which is made incident on the photonic crystal fiber 23, to thereby emit coherent white due to optical non-linear effect. Therefore, light with a desired wavelength may be taken out with the use of the line filter 24 from the white light thus emitted, which allows the probe light source 21 to be used as a kind of monochromatic ultra-short pulse laser.

In this embodiment, a Ti:sapphire pulse laser on the order of femtoseconds or picoseconds, or an Nd:YAG pulse laser on the order of nanosecond is used as the excitation light source 22 of the supercontinuum laser. Then, the white light from the supercontinuum laser source is adjusted to be in a linearly-polarized state, so that light with a wavelength of, for example, 1260 nm is selected through the line filter 24. This configuration allows selective derivation of CARS signals resulting from the fundamental vibration of a CH chemical group of an organic molecule.

The probe light emitted from the probe light source 21 is, similarly to the pump light, converted into circularly-polarized light by a quarter wavelength plate 25 serving as a polarization element, and further converted into a Laguerre-Gaussian beam by a phase plate 26 serving as a phase modulation element which is similarly configured as the phase plate 13, so as to be incident on a beam combiner 31.

Figure 8:
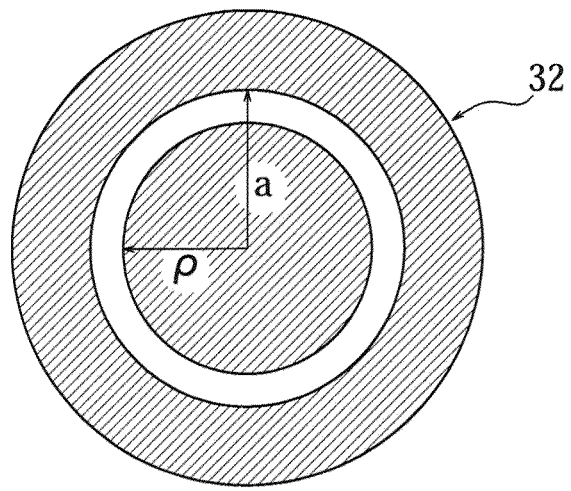
FIG. 8 is an enlarged plan view illustrating a schematic configuration of an example of the annular filter of FIG. 6.

The pump light and the probe light incident on the beam combiner 31 are coaxially synthesized by the beam combiner 31, which is then subjected to pupil operation through an annular filter 32 serving as a mask filter in an annular shape, and thereafter passes through an objective lens 33 to be collected onto a sample 35 placed on a sample stage 34 movable in each of the x, y, z axes directions. Here, as illustrated in an enlarged plan view of FIG. 8, the annular filter 32 is formed of, for example, a glass substrate on which chrome is vapor-deposited so as to cut off optical components at the optical axis center portion. In this embodiment, the annular filter 32 has a light shielding rate set to 0.8, which means that the ratio between the radius a of the pupil plane and the radius $\rho$ of the light shielding region is defined as $\rho/a=0.8$. Further, the objective lens 33 may have a numerical aperture set to, for example, 0.9.

The sample 35, which is irradiated with the pump light and the probe light, generates CARS signal light, which is converted into parallel light beams by a collimator lens 41 and then collected onto a confocal pinhole 43 by a condenser lens 42 so as to be incident on a spectrometer 44. Then, the light is dispersed in the spectrometer 44, and desired wavelength components are taken out through a spectrometer slit 45 and detected in a photomultiplier tube 46. Here, the confocal pinhole 43 functions a spatial filter and also has a function of improving the CARS signal light in monochromaticity.

When imaging the sample 35 by using the CARS signal light, the sample stage 45 is mapped while being spatially scanned. For example, an ordinary microscopic image can be obtained through flatbed scanning of the stage. This embodiment includes the confocal pinhole 43, and is therefore capable of obtaining a cross-sectional image in the depth direction by spatially-scanning the sample stage 34 in the optical axis (z) direction.

Therefore, in FIG. 6, the pump light source 11, the quarter wavelength plate 12, the phase plate 13, the probe light source 21, a quarter wavelength plate 25, a phase plate 26, the beam combiner 31, the annular filter 32, and the objective lens 33 form an illuminating part. Further, the collimator lens 41, the condenser lens 42, the confocal pinhole 43, the spectrometer 44, the spectrometer slit 45, and the photomultiplier tube 46 form a detecting part.

In the above-mentioned configuration, the Laguerre-Gaussian function to be obtained when pupil operation is performed by the annular filter 32 with consideration of the polarization component is mathematically formulated (see, for example, JP 3350442 (B2)). Therefore, the intensity distribution of electric field components in the z-axis direction on a focal plane can be calculated using the Laguerre-Gaussian function. Accordingly, an effective point spread functions can be obtained from Expression (1).

Figure 9:
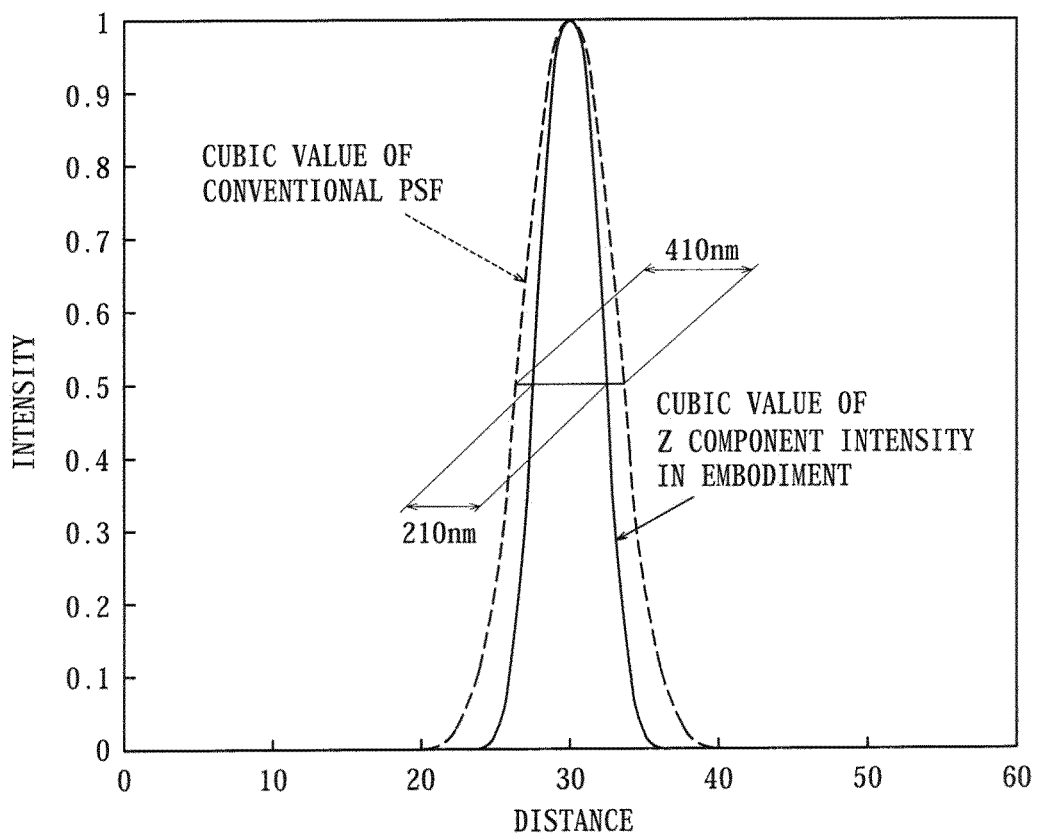
FIG. 9 is a graph showing, in comparison, point spread functions each obtained by the CARS microscope according to the embodiment of the present invention and by a conventional CARS microscope, respectively.

FIG. 9 is a graph showing, in comparison, a point spread function obtained by the CARS microscope according to the embodiment of the present invention and a point spread function obtained by a conventional CARS microscope. As is apparent from FIG. 9, the full width at half maximum of the point spread function, which shows a cubic value of the light-collecting intensity, is about 410 nm in the case of the conventional CARS microscope while being reduced to substantially half thereof to 210 nm in the case of the CARS microscope of this embodiment. This value is obviously above the diffraction limit that is conceivable by the classic wave optics, which produces a kind of super-resolution effect.

Further, the objective lens 33 can be replaced by an oil immersion lens to improve the numerical aperture up to 1.45, to thereby narrow down the full width at half maximum to about 130 nm. The resolution thus obtained is higher than that of an ordinary optical microscope. Therefore, according to this embodiment, in addition to the function of analyzing and visualizing the chemical structure of the sample 35, a super-resolution function can also be simultaneously derived.

Further, the CARS microscope according to this embodiment is capable of automatically adding a secondary function of, for example, improving S/N ratio, which is indispensable in microscopic observation. That is, it is known that the annular filter 32 inserted in an illumination system is capable of removing the non-resonant CARS signal which otherwise constitutes a background signal (see, for example, Appl. Phys. Lett. 97(2010)083701), which enables accurate detection of the resonance CARS signal resulting from the fundamental vibration of a CH chemical group.

Figure 10:
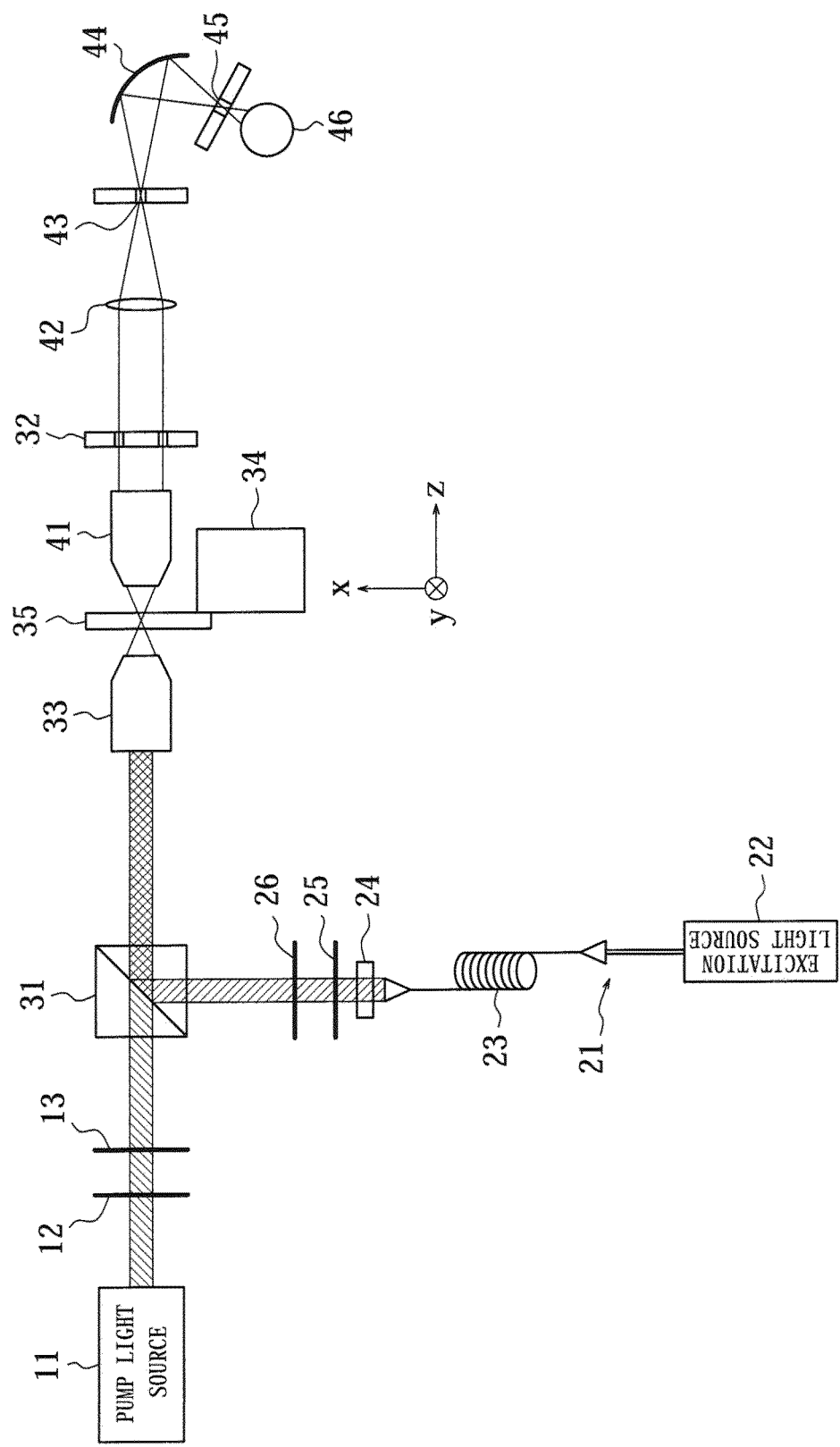
FIG. 10 illustrates a modified example of the CARS microscope of FIG. 6.

It should be noted that the present invention is no way limited to the above-mentioned embodiments, and may be subjected to various modifications and alterations. For example, the annular filter 32 is not particularly limited to the one inserted in an illumination system, and may be inserted in a detection optical system as illustrated in FIG. 10 to obtain the same effect. Therefore, the annular filter 32 may be inserted anywhere appropriately selected according to the geometry of the microscope.

Figure 11:
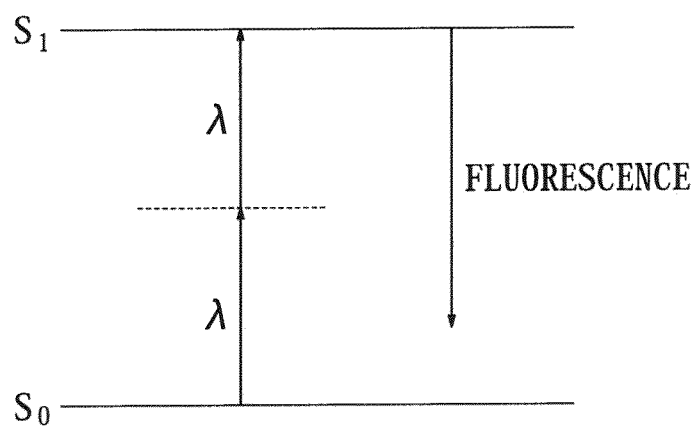
FIGS. 11(a) and 11(b) each illustrate two-photon absorption process in a two-photon microscope that uses a monochromatic light and in a multiples two-phonon microscope according to the present invention, respectively.
Figure 11:
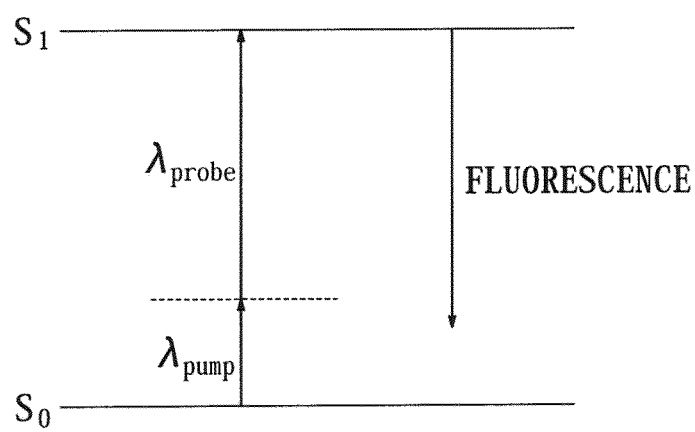

Further, the present invention can be applied, not only to the CARS microscope, but also to a CSRS microscope and to a multiplexed multiphoton microscope. For example, an ordinary two-photon microscope that uses monochromatic light employs a Ti:sapphire pulse laser of femtoseconds, and, as illustrated in FIG. 11(a), two photons of the same wavelength are absorbed at once from the ground state $S_0$ to the electronic excited state $S_1$ to thereby detect a fluorescent signal from $S_1$. In contrast, a multiphoton microscope according to the present invention uses two light sources for two colors of light, namely, $\lambda_{pump}$ and $\lambda_{probe}$ which are different from each other in wavelength, and, for example, as illustrated in FIG. 11(b), two photons of $\lambda_{pump}$ and $\lambda_{probe}$ which are different from each other in wavelength are absorbed from $S_0$ to $S_1$, to thereby detect a fluorescent signal from $S_1$. This configuration corresponds to a multiplexed two-photon microscope.

In this case, the sum of the energy of the two photons to be used needs to be equal to the excitation energy from $S_0$ to $S_1$. Further, similarly to the CARS microscope, the two color light beams need to be polarized in the same direction. With this configuration, fluorescence can be generated only from a region where the electric field components in the z direction, in which the two color light beams are always in the same polarization direction, overlap each other. In other words, in the microscope configuration illustrated in FIG. 6 or FIG. 10, the wavelength of the light source 11 or 21 may be adjusted to thereby form a multiplexed two-photon microscope, which enables detection of fluorescent signals at spatial resolution higher than the classic diffraction limit.

Figure 12:
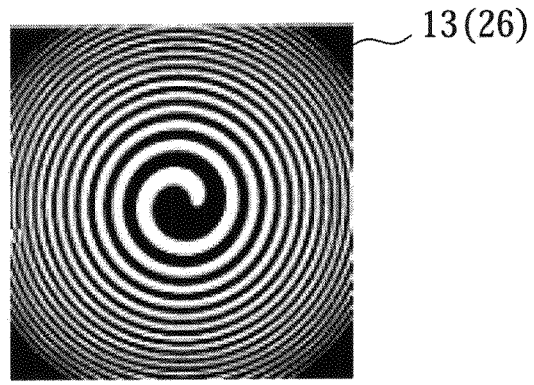
FIG. 12 illustrates a modified example of the phase plate of FIG. 6 or FIG. 10.
Figure 13:
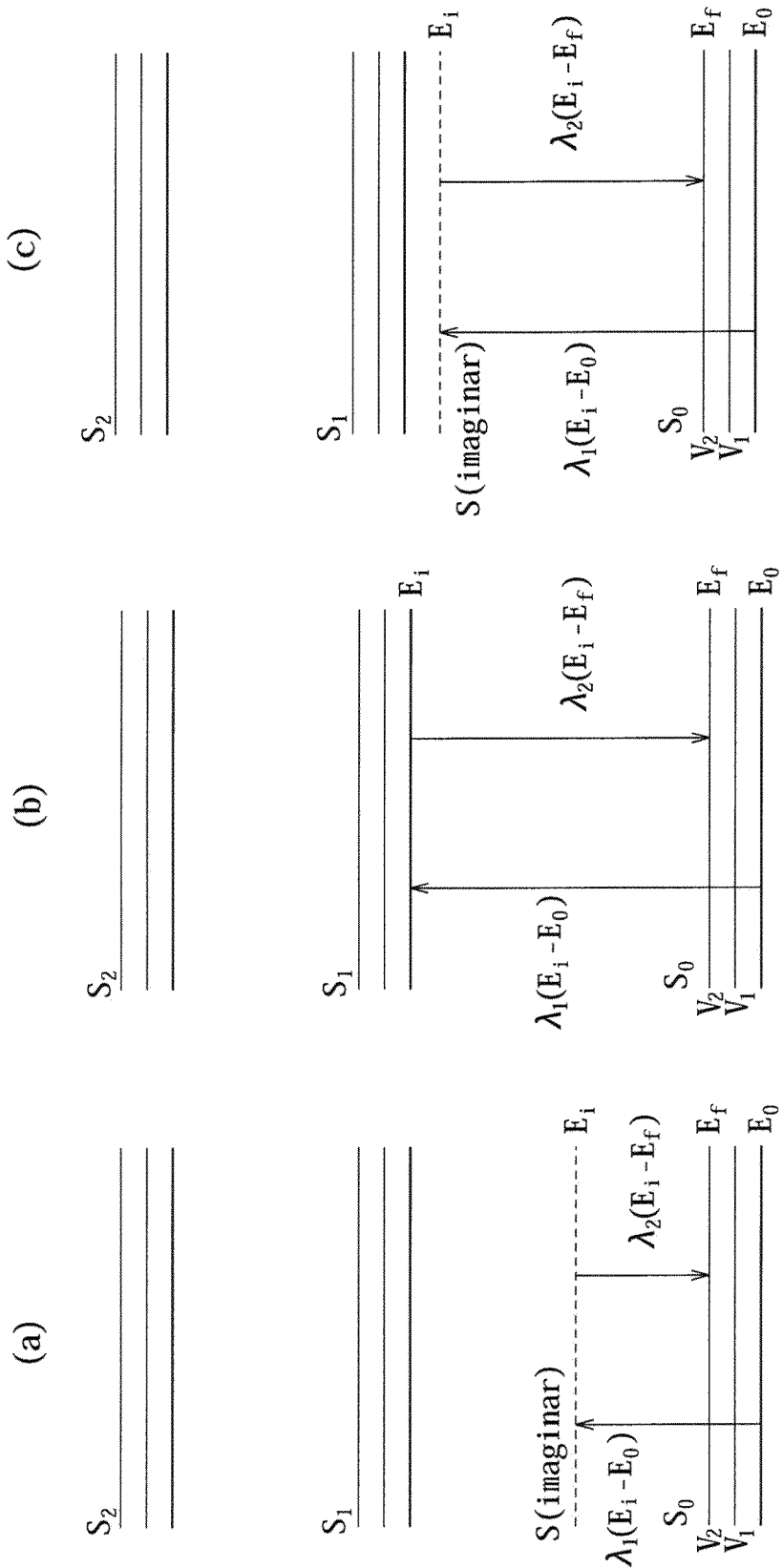
FIGS. 13(a) to 13(c) are energy diagrams each for illustrating non-resonant Raman scattering, true resonance Raman scattering, and preresonance Raman scattering, respectively.
Figure 14:
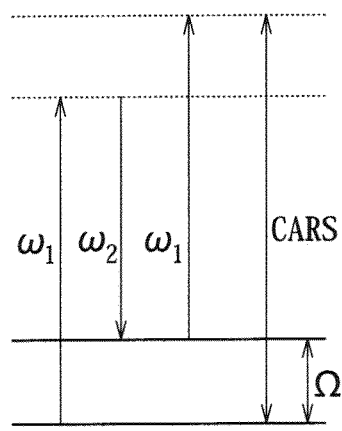
FIGS. 14(a) and 14(b) are energy diagrams each for illustrating coherent Raman scattering.
Figure 14:
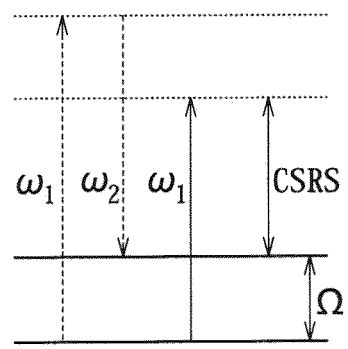

Further, in the configuration illustrated in FIG. 6 or FIG. 10, the phase plates 13, 26 each for converting pump light and probe light, respectively, into a Laguerre-Gaussian beam may be formed of a zone plate which includes a spiral orbit as illustrated in FIG. 12. In this case, the orbit may be changed in rotation direction thereof, to thereby control the rotation direction of the phase of the Laguerre-Gaussian beam (see, for example, Opt. Rev. 17(2010)79).

Further, the present invention can also be applied to a multiplex CARS microscope using three-color illumination light (see, for example, ultrabroadband multiplex CARS microspectroscopy using a supercontinuum light source. Hideaki Kano and Hiro-o Hamaguchi, ICORS2006, Yokohama (2006 August)), to thereby further improve the ability to identify chemical compositions.

As described above, the present invention is capable of improving an absolute resolution of a microscope including the CARS microscope, which uses a nonlinear optical process. In particular, in the CARS microscope, the present invention is capable of fulfilling all the ideal features as an optical microscope, namely, (1) no stain, (2) function of analyzing chemical composition, (3) super-high resolution, and (4) high S/N ratio, to thereby provide a microscope system capable of satisfying the demands of many microscope users.

DESCRIPTION OF NUMERALS 11 pump light source
12 quarter wavelength plate
13 phase plate
21 probe light source 22 excitation light source
23 photonic crystal fiber
24 line filter
25 quarter wavelength plate
26 phase plate
31 beam combiner
32 annular filter
33 objective lens
34 sample stage
35 sample
41 collimator lens
42 condenser lens
43 confocal pinhole
44 spectrometer
45 spectrometer slit
46 photomultiplier tube

The invention claimed is:

1. A nonlinear optical microscope, comprising:
an illuminating part, which includes an objective lens, for collecting a first illumination light beam and a second illumination light beam that overlap each other spatially and temporally, through the objective lens, onto a sample; and
a detecting part for detecting a signal light generated from the sample due to a nonlinear optical effect, the signal light resulting from collecting the first and second illumination light beams onto the sample,
wherein the second illumination light beam has a wavefront distribution different from a wavefront distribution of the first illumination light beam.

2. The nonlinear optical microscope according to claim 1, wherein the detecting part detects the signal light generated from the sample due to at least one of nonlinear optical effects including multiphoton excitation, Coherent Anti-Stokes Raman Scattering, and Coherent Stokes Raman Scattering.

3. The nonlinear optical microscope according to claim 1, wherein the illuminating part includes a phase modulation element and a polarization element, the phase modulation element modulating each of the first and second illumination light beams to be irradiated onto the sample into a Laguerre-Gaussian beam, and the polarization element polarizing each of the first and second illumination light beams to be irradiated onto the sample into a circularly-polarized or linearly-polarized light beam.

4. The nonlinear optical microscope according to claim 1, wherein the illuminating part includes a mask filter in an annular shape, the mask filter being disposed in an optical path along which the first and second illumination light beams are made incident as spatially and temporally overlapping each other.

5. The nonlinear optical microscope according to claim 1, wherein the detecting part includes:
a collimator lens for converting the signal light generated from the sample into parallel light beams; and
a mask filter in an annular shape disposed in an optical path of the parallel light beams, and detects the signal light passing through the mask filter.

6. Nonlinear optical microscopy, comprising:
an illuminating step of collecting a first illumination light beam and a second illumination light beam that overlap each other spatially and temporally, through an objective lens, onto a sample; and
a detecting step of detecting a signal light generated from the sample due to a nonlinear optical effect, the signal light resulting from collecting the first and second illumination light beams onto the sample,
wherein the second illumination light beam has a wavefront distribution different from a wavefront distribution of the first illumination light beam.

7. The nonlinear optical microscopy according to claim 6, wherein the detecting step includes detecting the signal light generated from the sample due to at least one of nonlinear optical effects including multiphoton excitation, Coherent Anti-Stokes Raman Scattering, and Coherent Stokes Raman Scattering.

8. The nonlinear optical microscopy according to claim 6, wherein each of the first and second illumination light beams to be irradiated onto the sample in the illuminating step is a Laguerre-Gaussian beam.

9. The nonlinear optical microscopy according to claim 6, wherein each of the first and second illumination light beams to be irradiated onto the sample in the illuminating step is an annular illumination light beam.

10. The nonlinear optical microscopy according to claim 6, wherein each of the first and second illumination light beams to be irradiated onto the sample in the illuminating step is a circularly-polarized or linearly-polarized light beam.

11. The nonlinear optical microscopy according to claim 6, wherein the detecting step includes detecting the signal light generated from the sample by a confocal method.

12. The nonlinear optical microscope according to claim 2, wherein the first illumination light beam is a pump light and the second illumination light beam is a probe light, and
wherein the detecting part detects the signal light generated from the sample due to a Coherent Stokes Raman Scattering effect, the signal light resulting from collecting the first and second illumination light beams onto the sample.

13. The nonlinear optical microscope according to claim 3, wherein the polarization element polarizes each of the first and second illumination light beams into a circularly-polarized light beam, so that an electric field of the first illumination light beam and an electric field of the second illumination light beam have different rotational speeds at a position where the first and second illumination light beams are collected.

14. The nonlinear optical microscope according to claim 3, wherein at a light-collecting point where the first and second illumination light beams are collected, a direction of an electric field component of the first illumination light beam that is parallel to an optical axis of the objective lens is identical to a direction of an electric field component of the second illumination light beam that is parallel to the optical axis of the objective lens, and a direction of an electric field component of the first illumination light beam that is perpendicular to the optical axis of the objective lens is not identical to a direction of an electric field component of the second illumination light beam that is perpendicular to the optical axis of the objective lens.

15. The nonlinear optical microscope according to claim 3, wherein the polarization element polarizes each of the first and second illumination light beams into a circularly-polarized light beam, and
wherein a phase rotation direction of the Laguerre-Gaussian beam is opposite to a rotation direction of the circularly-polarized light beam.

16. The nonlinear optical microscopy according to claim 7, wherein the first illumination light beam is a pump light and the second illumination light beam is a probe light, and
wherein the detecting step includes detecting the signal light generated from the sample due to a Coherent Stokes Raman Scattering effect, the signal light resulting from collecting the first and second illumination light beams onto the sample.

17. The nonlinear optical microscopy according to claim 10, wherein each of the first and second illumination light beams is polarized into a circularly-polarized light beam, so that an electric field of the first illumination light beam and an electric field of the second illumination light beam have different rotational speeds at a position where the first and second illumination light beams are collected.

18. The nonlinear optical microscopy according to claim 17, wherein at the position where the first and second illumination light beams are collected, a direction of an electric field component of the first illumination light beam that is parallel to an optical axis of the objective lens is identical to a direction of an electric field component of the second illumination light beam that is parallel to the optical axis of the objective lens, and a direction of an electric field component of the first illumination light beam that is perpendicular to the optical axis of the objective lens is not identical to a direction of an electric field component of the second illumination light beam that is perpendicular to the optical axis of the objective lens.

19. The nonlinear optical microscopy according to claim 8, wherein each of the first and second illumination light beams is polarized into a circularly-polarized light beam, and wherein a phase rotation direction of the Laguerre-Gaussian beam is opposite to a rotation direction of the circularly-polarized light beam.

\* \* \* \* \*